Nov. 26, 1935. R. T. MULLER Plant Pat. 150
ROSE
Filed March 11, 1935
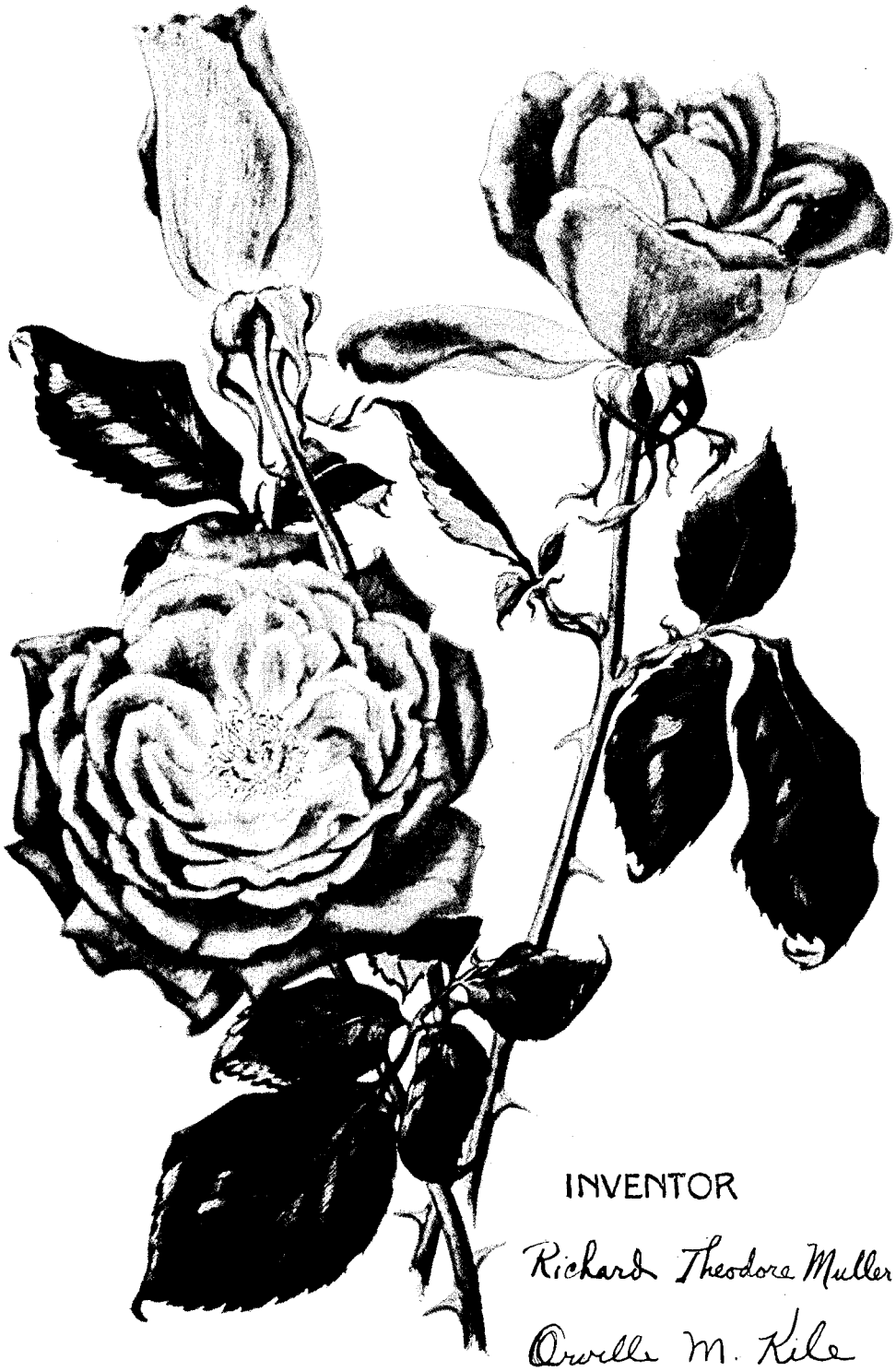
INVENTOR
Richard Theodore Muller
Orville M. Kile
PLANT PATENT AGENT Patented Nov. 26, 1935

Plant Pat. 150

UNITED STATES PATENT OFFICE

150

ROSE

Richard Theodore Muller, Amherst, Mass., assignor to The Montgomery Company, Incorporated, Hadley, Mass.

Application March 11, 1935, Serial No. 10,511

1 Claim. (Cl. 47—61)

My present invention consists of an improvement in red hybrid tea roses of the type intended principally for greenhouse commercial use. This new variety is a seedling developed through hybridization conducted by myself in 1931. It is a cross between the Hadley and the Talisman varieties of which the former is the seed parent and the latter the pollen parent. The seed germinated in March 1932.

In general this new variety resembles Hadley but is much brighter and lighter in color. Its Talisman parentage is also apparent in the yellow to orange color at the base of the petals, particularly in the bud, and by the slight diffusion of yellow into the red of the petals, giving a slight orange glow which is very desirable.

The accompanying illustrations shown in full color and in approximately natural size an opening bud, a half opened flower, and a fully opened flower, also typical stems and foliage.

The following is a detailed description of this variety;

*The plant.*—Grows about four feet high under normally favorable conditions, is a fairly vigorous grower, resistant to disease, and new growth starts quickly after cutting back. It produces less blind wood than Hadley. The plant produces an abundance of flowers and ample foliage.

*Foliage.*—Leaves are of medium size, of vigorous, somewhat glossy appearance and "Elm Green" in color, according to Plate XVII of Ridgway's Color Standards and Nomenclature.

The edges of the leaves are rather deeply notched. The rachises of the compound leaves bear 1 to 3 rather large thorns. The foliage has a more vigorous and healthy appearance than that of the variety Hadley.

*Stems.*—Are medium to heavy, zig-zag rather than straight, and while the peduncles (3 to 4 inches) are free of thorns the lower stems are beset with long, large and numerous dark colored thorns, in this latter respect materially differing from Hadley.

*Hips.*—Rather small and tapering.

*Sepals.*—Mostly simple but on some specimens foliaceous.

*Stipules.*—Rather wide and having sharp points only slightly inclined to curl.

*Buds.*—Long and somewhat urn-shaped when opening. The sepals curl back early, showing the cadmium color at the base of the petals.

*Blossoms.*—In the opening bud the predominant effect is nearer Tyrian Rose (Plate XII) than any other color shown in Ridgway's Color Standards and Nomenclature. The outside (underneath) surfaces of most outer petals have a slightly purplish tone except toward the base where a slight diffusion of shades of orange (Cadmium Orange—Plate III) are seen. This orange shade becomes more intense as the base of the petal is reached. This discloses its Talisman parentage.

The inside surface of the petals (in this stage) are a richer, brighter shade—more nearly a Carmine (Plate I) but far brighter and somewhat lighter than the "Carmine" shown in the color guide.

The velvety inner surface gives great richness to the color and a variety of shades in the different lights caught by various portions of the petals.

When fully opened, the blossoms are usually 5 inches across, almost perfectly formed, with full petallage evenly distributed, having about 40 petals in early November. Each petal curls back at the outer edge, on two to three axes, forming pointed effects, but the curling takes place only at the edges. This curling is most pronounced on the outermost rows of petals and disappears as the innermost petals are reached.

As the blossoms open out and the petals curl back, the color effect changes because of the exposure of the inside surface of the petals rather than the outside as shown in the buds. Ridgway's Color Standards and Nomenclature simply fails to show any color or shade even near that of this rose. The nearest it can be described by comparison with Ridgway's is as between Tyrian Rose and Amaranth Purple (Plate XII), but bright and velvety as contrasted with the dull colors shown in the guide.

The blossoms open cleanly—no bull noses—and last well when used as cut flowers.

When fully opened the stamens and pistils are clearly disclosed. In fact they stand out rather prominently because of the orange or yellowish background provided by these colors on a small basal area of each petal.

The stamens are moderately numerous, reddish in color and surmounted by buff-colored anthers. The pistils are reddish colored, terminating in light colored stigmas. They arise from a distinct button-shaped pithy formation.

The flowers of this variety are moderately fragrant and have good keeping qualities.

Having thus fully described and disclosed my invention, I claim:

The variety of rose plant herein described and illustrated, characterized particularly by its vigorous, healthy growing qualities, the production of less blind wood and more thorns than the nearest similar variety, and by the production of flowers having a distinctive, rich, bright near-carmine color, as described, with cadmium-orange colors on the petal bases, and other desirable qualities.

RICHARD T. MULLER.